US006824979B2

(12) United States Patent
Phibbs et al.

(10) Patent No.: US 6,824,979 B2
(45) Date of Patent: Nov. 30, 2004

(54) **CATABOLITE REPRESSION CONTROL (CRC) GENE AND *PSEUDOMONAS* VIRULENCE**

(75) Inventors: Paul V. Phibbs, Greenville, NC (US); David N. Collier, Greenville, NC (US); Paul W. Hager, Greenville, NC (US)

(73) Assignee: East Carolina University, Greenville, NC (US)

(*) Notice: Subject to any disclaimer, the term of this patent is extended or adjusted under 35 U.S.C. 154(b) by 241 days.

(21) Appl. No.: 09/747,514

(22) Filed: Dec. 21, 2000

(65) Prior Publication Data

US 2002/0102628 A1 Aug. 1, 2002

(51) Int. Cl.[7] .................. C12Q 1/68; G01N 33/569; C12P 1/04
(52) U.S. Cl. .................. 435/6; 435/7.37; 435/170
(58) Field of Search .................. 435/6, 172.3, 325, 435/375, 91.1; 514/44; 536/24.5, 23.1, 27, 24.1, 24.3, 24.32

(56) References Cited

U.S. PATENT DOCUMENTS

| | | | |
|---|---|---|---|
| 5,989,912 A | 11/1999 | Arrow et al. | |
| 6,015,886 A | 1/2000 | Dale et al. | |
| 2002/0077272 A1 | * 6/2002 | Mahan et al. | .............. 514/1 |

FOREIGN PATENT DOCUMENTS

| | | | |
|---|---|---|---|
| WO | WO 98/03533 | * | 7/1997 |
| WO | WO 98/03533 | | 1/1998 |

OTHER PUBLICATIONS

Ch MacGregor et al., Journal of Bacteriology, "The Nucleotide Sequence of the *Pseudomonas aeruginosa* pyrE–crc–rph Region and the Purification of the crc Gene Product," Oct. 1996, vol. 178, No. 19, pp. 5627–5635.*
Ga O'Toole et al., Journal of Bacteriology, "The Global Carbon Metabolism Regulator Crc is a Component of a Signal Transduction Pathway Required for Biofilm Development by *Pseudomonas aeruginosa*," Jan. 2000, vol. 182, No. 2, pp. 425–431.*
Bd Bright et al., 96th ASM General Meeting, "crc Mutants of *P.aeruginosa* Have Aletations in the Production of Diverse Virulence Factors," May 1996, p. B–377.*
Bd Bright et al., 1995 Cystic Fibrosis Conference, "Involvement of the crc Locus in the Regulation of the Expression of *Pseudomonas aeruginosa* Virulence Factors,"Sep. 1995, p. 244.*
Wolf et al. Isolation and Characterization of Catabolite Repression Control Mutants of *Pseudomonas aeruginosa* PAO. Journa of Bacteriology, 1991 vol. 173:4700–4706.*
Symth et al. Catabolite Repression of *Pseudomonas aeruginosa* amidase: Isolation of Promoter Mutants.*
International Search Report for International application Ser. No. PCT/US01/51047 dated Aug. 9, 2002.

Bright et al., *Involvement of the crc Locus in the Regulation of the Expression of Pseudomonas aeruginosa Virulence Factors*, 231, 1995 Cystic Fibrosis Conference, pp. 244 (1995).
Phibbs et al., *crc Mutants of P.aeruginosa Have Alterations in the Production of Diverse Virulence Factors*, B–377, 96th ASM General Meeting, pp. 220 (May 1996).
Collier, et al., *Isolation and Characterization of Pseudomonas aeruginosa Mutants Containing Suppressors of Defective crc Alleles*, K–94, Microbial Physiology and Metabolism, 97th ASM General Meeting, pp. 357 (May 1997).
Hester, et al., *Crc is Involved in Catabolite Repression Control of the bkd Operons of Pseudomonas putida and Pseudomonas aeruginosa*, vol. 182, No. 4, Journal of Bacteriology, pp. 1144–1149 (Feb. 2000).
MacGregor, et al., *The Nucleotide Sequence of the Pseudomonas aeruginosa pyrE–crc–rph Region and the Purification of the crc Gene Product*, vol. 178, No. 19, pp. 5627–5635 (Oct. 1996).
Collier, et al., *Isolation and Characterization of Pseudomonas aeruginosa Mutants Containing Suppressors of Defective crc Alleles*, FEMS Microbiology Letters, vol. 196, pp. 87–92 (2001).
Breithaupt, Holger, *The new antibiotics—Can novel antibacterial treatments combat the rising tide of drug–resistant infections?*, Nature Biotechnology, vol. 17, pp. 1165–1169 (Dec. 1999).
Larsen, H. Jakob, et al., *Antisense properties of peptide nucleic acid*, Biochimica et Biophysica Acta, col. 1489, pp. 159–166 (1999).
White, D.G., et al., *Inhibition of the Multiple Antibiotic Resistance (mar) Operon in Escherichia coli by Antisense DNA Analogs*, Antimicrobial Agents and Chemotherapy, vol. 41, No. 12, pp. 2699–2704 (Dec. 1997).
Moellering, Robert C., *Antibiotic Resistance: Lessons for the Future*, Clinical Infectious Diseases, vol. 27 (Suppl 1), pp. S135–40 (1998).

(List continued on next page.)

*Primary Examiner*—Karen A. Lacourciere
*Assistant Examiner*—Terra C. Gibbs
(74) *Attorney, Agent, or Firm*—Myers Bigel Sibley & Sajovec

(57) ABSTRACT

The present invention relates to a method of screening for compounds that inhibit the virulence of *Pseudomonas* bacteria and comprises the steps of: providing a culture medium comprising *Pseudomonas* bacteria, administering a test compound to said bacteria, and then detecting the presence or absence of inhibition of the catabolite repression control (Crc) protein in the bacteria. The inhibition of the Crc protein indicates that the compound has antivirulence activity against *Pseudomonas* bacteria. Antisense oligonucleotides that inhibit expression of the Crc protein in a *Pseudomonas* bacteria and is nuclease resistant are also disclosed. Antivirulence compounds and the uses thereof in treating *Pseudomonas* infections are also disclosed.

9 Claims, No Drawings

OTHER PUBLICATIONS

MacGregor, C.H., et al., *Cloning of a Catabolite Repression Control (crc) Gene from Pseudomonas aeruginosa, Expressinof the Gene in Escherichia coli, and Identification of the Gene Product in Pseudomonas aeruginosa*, Journal of Bacteriology, vol. 173, No. 22, pp. 7204–7212 (Nov. 1991).

Wolff, J.A., et al., *Isolation and Characterization of Catabolite Repression Control Mutants of Pseudomonas aeruginosa PAO*, Journal of Bacteriology, vol. 173, No. 15, pp. 4700–4706 (Aug. 1991).

Collier, D.N., et al., *Catabolite repression control in the Pseudomonads*, Research in Microbiology—14th Forum in Microbiology, vol. 147, No. 6–7, pp. 551–561 (1996).

O'Toole, George A., et al., *The Global Carbon Metabolism Regulator Crc is a Component of a Signal Transductin Pathway Required for Biofilm Development by Pseudomonas aeruginosa*, Journal of Bacteriology, vol. 182, No. 2, pp. 425–431 (Jan. 2000).

* cited by examiner

CATABOLITE REPRESSION CONTROL (CRC) GENE AND *PSEUDOMONAS* VIRULENCE

FIELD OF THE INVENTION

The present invention concerns methods of screening for active agents useful as an antibacterial agent against *Pseudomonas*, as well as active agents and methods of use thereof in treating *Pseudomonas*.

BACKGROUND OF THE INVENTION

*Pseudomonas* infection is a leading cause of death in cystic fibrosis, and one of the top causes of serious hospital-acquired infections. *Pseudomonas* infection is particularly serious in burn victims and leukemia patients, and can cause blindness by infection in patients afflicted with trauma to the eye through surgery or contact lenses. Further, *Pseudomonas* has a high intrinsic resistance to current antibiotics. Hence, there is a need for the development of new antibiotics to treat *Pseudomonas* infections.

The use of antisense oligonucleotides in the treatment of bacterial infections is known. U.S. Pat. No. 5,294,533 to J. Lupski and L. Katz (assigned to Baylor College of Medicine and Abbott Laboratories, Inc.) describes a method of interrupting the expression of a macromolecular synthesis operon in bacteria comprising the step of binding an antisense oligonucleotide to a single stranded DNA or to a mRNA transcribed from the macromolecular synthesis operon. The antisense oligonucleotide can be either sequence specific to a unique intergenic sequence or a sequence specific to a bacterial homologous sequence. By interrupting the expression of the macromolecular synthesis, it is said that bacterial infections can be treated.

U.S. Pat. No. 6,060,241 to I. Corthesy-Theulaz (assigned to Kieta Holding SA) describes a poly-3-hydroxybutyrate metabolic pathway essential for *Helicobacter pylori* survival in a host. A *Helicobacter pylori* Coenzyme A transferase (Hp CoA-t), thiolase and PHB synthase, as well as methods for their preparation and use are provided. Pharmaceutical compositions containing Hp CoA-t protein fragments, antisense nucleic acids or other inhibitors of Hp CoA-t, thiolase and PHB synthase, as well as methods for their use in the treatment of some types of gastric disease are also described. This reference is not concerned with *Pseudomonas*.

PCT Application WO98/03533A1 to A. Arrow et al. (assigned to Oligos Etc. and Oligos Therapeutics Inc.) describes the general therapeutic use of nuclease resistant oligonucleotides for treating animals having an infection caused by a pathogenic bacterium. The method is a general one and involves the integration of (1) methods for selecting the correct oligonucleotide, (2) synthesis and purification of nuclease resistant oligonucleotides, and (3) methods for in vitro analysis of potential antimicrobial oligonucleotides.

There remains a need for new ways to screen for antibiotics effective against *Pseudomonas*, along with compounds and methods of treating *Pseudomonas* infections.

SUMMARY OF THE INVENTION

The present invention provides a method of screening for compounds that inhibit the virulence of *Pseudomonas* bacteria. The method comprises the steps of: providing a culture medium comprising *Pseudomonas* bacteria; administering a test compound to said bacteria; and then detecting the presence or absence of inhibition of the catabolite repression control (Crc) protein in said bacteria, the inhibition of the Crc protein indicating said compound has antivirulence activity against *Pseudomonas* bacteria.

A second aspect of the present invention is an antivirulence compound (for example, an antisense oligonucleotide) that inhibits expression or activity of the Crc protein in a *Pseudomonas* bacteria. Such compounds are useful as antivirulence compounds. When such compounds are antisense oligonucleotides they are preferably from 8 to 25, 40 or 80 nucleotides in length, and preferably are nuclease resistant.

A third aspect of the present invention is an antivirulence compound as described above in a pharmaceutically acceptable carrier.

A fourth further aspect of the present invention is a method of inhibiting the virulence of *Pseudomonas* bacteria, comprising administering to *Pseudomonas* bacteria an antivirulence compound as described above in an effective antivirulence amount. The administering step may be carried out in vitro, for example in drug testing or screening studies, or may be carried out in vivo in the treatment of a subject.

A further aspect of the present invention is a method of treating *Pseudomonas* infection in a subject in need thereof, comprising administering to said subject an antivirulence compound as described above in an amount effective to treat said *Pseudomonas* infection.

A still further aspect of the present invention is the use of an antivirulence compound as described above for the preparation of a medicament for carrying out a method as described above.

The foregoing and other objects and aspects of the present invention are explained in greater detail in the specification set forth below.

DETAILED DESCRIPTION OF THE PREFERRED EMBODIMENTS

The term "*Pseudomonas*" as used herein refers to any type of *Pseudomonas* bacteria, including but not limited to *Pseudomonas aeruginosa, Pseudomonas putida, Pseudomonas fluorescens,* and *Pseudomonas multivorans*. Particularly preferred for carrying out the present invention is *Pseudomonas aeruginosa*.

The terms "antivirulence" and "antivirulent" as used herein refers to the activity of a compound in reducing, at least in part, the degree of pathogenicity of a microorganism, as indicated by fatality rate of infected hosts infected with that microorganism and/or the ability of that microorganism to invade the tissues of an infected host.

The term "compound" as used herein refers to a peptide, peptidomimetic, organic, or other chemical molecule, and also refers to a nucleic acid molecule or chemical derivative thereof.

The term "oligonucleotide" herein includes naturally occurring, and modified nucleotides linked together by naturally occurring, and non-naturally occurring oligonucleotide linkages. Oligonucleotides are usually a polynucleotide subset with 200 bases or fewer in length. Preferably oligonucleotides are minimally 10 to 60 bases in length and most preferably 12, 13, 14, 15, 16, 17, 18, 19, or 20 to 40 bases in minimal length. Oligonucleotides are usually single-stranded, e.g. for probes; although oligonucleotides may be double-stranded, e.g. for use in the construction of a gene mutant. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoraniladate, phosphoroamidate, and the like. An oligonucleotide can include a label for detection, if desired. Peptide nucleic acids (PNAs) are a specific example of oligonucleotides included within the term "oligonucleotide". Examples of peptide nucleic acid structures (in the appropriate sequence as given below), that may be used to carry out the present invention include, but are not limited to, those described in U.S. Pat. Nos. 5,986,053; 6,133,444; 6,107,470; 6,015,887; 6,015,710; 5,846,010; 5,773,571; 5,672,584; 5,539,083; and 5,539,082 (applicants specifically intend that the disclosures of all United States patent references cited herein are to be incorporated by reference herein in their entirety).

Subjects with which the present invention is concerned include both human subjects and animal subjects (particularly mammalian subjects such as dogs, cats, horses, cattle) for veterinary purposes.

1. Screening Methods.

Test compounds, including combinatorial libraries of such compounds, that may be screened for activity by the methods of the invention are, in general, small organic compounds (i.e., non-oligomers), oligomers, or combinations thereof. Compounds which exhibit activity in these methods are referred to as "active compounds" below.

Small organic compounds (or "non-oligomers") include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, terpenes, porphyrins, toxins, catalysts, as well as combinations thereof. Libraries of such compounds are available, examples including benzodiazepine libraries as described in U.S. Pat. No. 5,288,514; phosphonate ester libraries as described in U.S. Pat. No. 5,420,328, pyrrolidine libraries as described in U.S. Pat. Nos. 5,525,735 and 5,525,734, and diketopiperazine and diketomorpholine libraries as described in U.S. Pat. No. 5,817,751.

Oligomers include oligopeptides, oligonucleotides, oligosaccharides, polylipids, polyesters, polyamides, polyurethanes, polyureas, polyethers, and poly (phosphorus derivatives), e.g. phosphates, phosphonates, phosphoramides, phosphonamides, phosphites, phosphinamides, etc., poly (sulfur derivatives) e.g., sulfones, sulfonates, sulfites, sulfonamides, sulfenamides, etc., where for the phosphorous and sulfur derivatives the indicated heteroatom for the most part will be bonded to C, H, N, O or S, and combinations thereof. Such oligomers may be obtained from combinatorial libraries in accordance with known techniques, or may be designed to have an antisense sequence based upon the known sequence of the Crc gene, such as assigned GenBank accession number L12038 (C. MacGregor et al., *J. Bacteriol.* 178, 5627–5635 (1996). Examples of such oligonucleotides include, but are not limited to, those having the sequence given herein as SEQ ID NO:1, SEQ ID NO: 2, SEQ ID NO: 3, and SEQ ID NO: 4.

As noted above, a method of screening for compounds that inhibit the virulence of *Pseudomonas* bacteria comprises first providing a culture medium comprising *Pseudomonas* bacteria and administering a test compound to said bacteria. The bacterial culture can be provided in any suitable form, such as in a petri dish on a growth medium, and the test compound can be administered to the bacterial culture in any way, such as by diluting the test compound and applying it to colonies of bacteria on a petri dish; mixing bacteria in a solution containing the test compound and then applying those bacteria to a culture medium in a petri dish; etc.

The step of detecting the presence or absence of inhibition of the catabolite repression control (Crc) protein in the bacteria can be carried out directly (e.g., by the use of oligonucleotide probes for Crc gene expression activity; by isolation and quantification of expressed Crc protein) or indirectly (e.g., by observation of responses mediated by the Crc gene and encoded protein). It will be noted that the detecting step is a selective one: that is, the test compound is not applied in an antibacterial amount to the bacteria, as this would prevent the identification of compounds that selectively inhibit the Crc protein.

A particularly suitable screening assay is one in which fluoroacetamide is used in the bacterial culture. Fluoroacetamide is ordinarily metabolized to fluoroacetic acid by amidase in *Pseudomonas* bacteria, with the fluoroacetic acid being toxic to the bacteria. Amidase operon repressors, which are mediated by crc, reduce the amount of amidase in the cells and thus protect the cells from fluoroacetic acid toxicity. Any suitable amidase operon repressor can be used, including Krebs cycle intermediates and acetate, with succinic acid particularly preferred. Thus, test compounds that inhibit the crc protein can be detected by adding an amidase operon repressor to the culture medium, adding fluoroacetamide to the culture medium, and administering the test compound to the bacteria. Detection of crc inhibition can then be carried out by detecting the poisoning of said bacteria (e.g., death of bacteria, inibition of bacterial growth or function, etc.) by the fluoroacetamide (specifically, by its toxic degradation product fluoroacetic acid). The poisoning of the bacteria by the fluoroacetamide indicates the test compound has antivirulence activity against *Pseudomonas* bacteria.

2. Active Compounds and Pharmaceutical Formulations.

Active compounds (or "antivirulence compounds") of the present invention are compounds that exhibit antivirulence activity in the screening procedures described above. Such compounds may be oligomers (including antisense oligonucleotides) or nonoligomers.

Antisense oligonucleotides of the invention may comprise any polymeric compound capable of specifically binding to a target polynucleotide by way of a regular pattern of monomer-to-nucleoside interactions, such as Watson-Crick type of base pairing, Hoogsteen or reverse Hoogsteen types of base pairing, or the like. Antisense compounds of the invention may also contain pendent groups or moieties, either as part of or separate from the basic repeat unit of the polymer, to enhance specificity, nuclease resistance, delivery, or other property related to efficacy, e.g. cholesterol moieties, duplex intercalators such as acridine, poly-L-lysine, "end capping" with one or more nuclease-resistant linkage groups such as phosphorothioate, and the like. Thus, numerous different "backbone" chemistries, including the peptide nucleic acid chemistries, can be used for the oligonucleotides, as long as the desired or necessary sequence is incorporated into the particular molecule used.

Antisense compounds of the invention include the pharmaceutically acceptable salts thereof, including those of alkaline earths, e.g. sodium or magnesium, ammonium or $NX_4+$, wherein X is $C_1$–$C_4$ alkyl. Other pharmaceutically acceptable salts include organic carboxylic acids such as acetic, lactic, tartaric, malic, isethionic, lactobionic, and succinic acids; organic sulfonic acids such as methanesulfonic, ethanesulfonic, and benzenesulfonic; and inorganic acids such as hydrochloric, sulfuric, phosphoric, and sulfamic acids. Pharmaceutically acceptable salts of a compound having a hydroxyl group include the anion of such compound in combination with a suitable cation such as Na+, $NH_4$+, or the like.

Preferably, nuclease resistance is conferred on the antisense compounds of the invention by providing nuclease-resistant internucleosidic linkages. Many such linkages are known in the art, e.g. phosphorothioate: Zon and Geiser, Anti-Cancer Drug Design, 6: 539–568 (1991); Stec et al, U.S. Pat. No. 5,151,510; Hirschbein, U.S. Pat. No. 5,166,387; Bergot, U.S. Pat. No. 5,183,885; phosphorodithioates: Marshall et al, Science, 259:1564–1570 (1993); Carathers and Nielsen, International application PCT/US89/02293; phosphoramidates, e.g. —OP(=O)($NR^1$ $R^2$)—O— with $R^1$ and $R^2$ hydrogen or $C_1$–$C_3$ alkyl: Jager et al, Biochemistry, 27:7237–7246 (1988); Froehler et al, International application PCT/US90/03138; peptide nucleic acids: Nielsen et al, Anti-cancer Drug Design, 8: 53–63 (1993), International application PCT/EP92/01220; methylphosphonates: Miller et al, U.S. Pat. No. 4,507,433; Ts'o et al, U.S. Pat. No. 4,469,863; Miller et al, U.S. Pat. No. 4,757,055; and P-chiral linkages of various types, especially phosphorothioates, Stec et al, European patent application 92301950.9 and Lesnikowski, Bioorganic Chemistry, 21:127–155 (1993). Additional nuclease linkages include phosphoroselenoate, phosphorodiselenoate, phosphoroanilothioate, phosphoranilidate, alkylphosphotriester such as methyl- and ethylphosphotriester, carbonate such as carboxymethyl ester, carbamate, morpholino carbamate, 3'-thioformacetal, silyl such as dialkyl ($C_1$–$C_6$)- or diphenylsilyl, sulfamate ester, and the like. Such linkages and methods for introducing them into oligonucleotides are described in many references, e.g. reviewed generally by Peyman and Ulmann (cited above); Milligan et al (cited above); Matteucci et al, International application PCT/US91/06855. Preferably, phosphorus analogs of the phosphodiester linkage are employed in the compounds of the invention, such as phosphorothioate, phosphorodithioate, phosphoramidate, or methylphosphonate. More preferably, phosphorothioate is employed as the nuclease resistant linkage. It is understood that in addition to the preferred linkage groups, compounds of the invention may comprise additional modifications, e.g. boronated bases, Spielvogel et al, U.S. Pat. No. 5,130,302; cholesterol moieties, Shea et al, Nucleic Acids Research, 18:3777–3783 (1990) or Letsinger et al, Proc. Natl. Acad. Sci., 86:6553–6556 (1989); 5-propenyl modification of pyrimidines, Froehler et al, Tetrahedron Lett., 33: 5307–5310 (1992); and the like.

Other examples of antisense oligonucleotides (i.e., chemical backbone structures) that may be used to carry out the present invention include those described in U.S. Pat. No. 6,015,866 to Arrow and U.S. Pat. No. 5,989,912 to Arrow.

Preferably, antisense compounds of the invention are synthesized by conventional means on commercially available automated DNA synthesizers, e.g. an Applied Biosystems (Foster City, Calif.) model 380B, 392 or 394 DNA/RNA synthesizer. Preferably, phosphoramidite chemistry is employed, e.g. as disclosed in the following references: Beaucage and Iyer, Tetrahedron, 48:2223–2311 (1992); Molko et al, U.S. Pat. No. 4,980,460; Koster et al, U.S. Pat. No. 4,725.677; Caruthers et al, U.S. Pat. Nos. 4,415,732; 4,458,066; and 4,973,679; and the like.

In embodiments where triplex formation is desired, there are constraints on the selection of target sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g. whether ribose or deoxyribose nucleosides are employed), base modifications (e.g. methylated cytosine, and the like) in order to maximize, or otherwise regulate, triplex stability as desired in particular embodiments, e.g. Roberts et al, Proc. Natl. Acad. Sci., 88:9397–9401 (1991); Roberts et al, Science, 258:1463–1466 (1992); Distefano et al, Proc. Natl. Acad. Sci., 90:1179–1183 (1993); Mergny et al, Biochemistry, A 30:9791–9798 (1991); Cheng et al, I. Am. Chem. Soc., 114:4465–4474 (1992); Beal and Dervan, Nucleic Acids Research, 20:2773–2776 (1992); Beal and Dervan, 1. Am. Chem. Soc., 114:4976–4982 (1992); Giovannangeli et al, Proc. Natl. Acad. Sci., 89: 8631–8635 (1992); Moser and Dervan, Science, 238:645–650 (1987); McShan et al, J. Biol. Chem., 267:5712–5721 (1992); Yoon et al, Proc. Natl. Acad. Sci., 89:3840–3844 (1992); Blume et al, Nucleic Acids Research, 20:1777–1784 (1992); and the like.

The length of the oligonucleotide moieties is sufficiently large to ensure that specific binding will take place only at the desired target polynucleotide and not at other fortuitous sites, as explained in many references, e.g. Rosenberg et al, International application PCT/US92/05305; or Szostak et al, Meth. Enzymol. 68:419–429 (1979). The upper range of the length is determined by several factors, including the inconvenience and expense of synthesizing and purifying oligomers greater than about 30–40 nucleotides in length, the greater tolerance of longer oligonucleotides for mismatches than shorter oligonucleotides, whether modifications to enhance binding or specificity are present, whether duplex or triplex binding is desired, and the like. Usually, antisense compounds of the invention have lengths in the range of about 12 to 60 nucleotides. More preferably, antisense compounds of the invention have lengths in the range of about 15 to 40 nucleotides; and most preferably, they have lengths in the range of about 18 to 30 nucleotides.

The antisense oligonucleotides of the invention can be synthesized by any of the known chemical oligonucleotide synthesis methods. Such methods are generally described, for example, in Winnacker, From Genes to Clones: Introduction to Gene Technology. VCH Verlagsgesellschaft mbH (H., Ibelgaufts trans. 1987). Any of the known methods of oligonucleotide synthesis can be utilized in preparing the instant antisense oligonucleotides. The antisense oligonucleotides are most advantageously prepared by utilizing any of the commercially available, automated nucleic acid synthesizers. The device utilized to prepare the oligonucleotides described herein, the Applied Biosystems 380B DNA Synthesizer, utilizes β-cyanoethyl phosphoramidite chemistry.

Oligonucleotides complementary to and hybridizable with any portion of the Crc gene mRNA transcript are, in principle, effective for inhibiting translation of the transcript, and capable of inducing the effects herein described. Translation is most effectively inhibited by blocking the mRNA at a site at or near the initiation codon. Thus, oligonucleotides complementary to the 5'-terminal region of the Hp CoA-t or thiolase mRNA transcript are preferred. Secondary or tertiary structure which might interfere with hybridization is minimal in this region. The antisense oligonucleotide is preferably directed to a site at or near the ATG initiation codon for protein synthesis. Oligonucleotides complementary to a portion of the Hp CoA-t or thiolase mRNA including the initiation codon are preferred. While antisense oligomers complementary to the 5'-terminal region of the Hp CoA-t or thiolase transcript are preferred, particularly the region including the initiation codon, it should be appreciated that useful antisense oligomers are not limited to those complementary to the sequences found in the translated portion of the mRNA transcript, but also includes oligomers complementary to nucleotide sequences contained in, or extending into, the 5'- and 3'-untranslated regions.

Preferably, the thermal stability of the antisense oligonucleotides of the invention are determined by way of melting, or strand dissociation, curves. The temperature of fifty percent strand dissociation is taken as the melting temperature, $T_m$, which, in turn, provides a convenient measure of stability. $T_m$ measurements are typically carried out in a saline solution at neutral pH with target and antisense oligonucleotide concentrations at between about 1.0–2.0 $\mu$M. Typical conditions are as follows: 150 mM NaCl and 10 mM $MgCl_2$ in a 10 mM sodium phosphate buffer (pH 7.0) or in a 10 mM Tris-HCl buffer (pH 7.0); or like conditions. Data for melting curves are accumulated by heating a sample of the antisense oligonucleotide/target polynucleotide complex from room temperature to about 85–90° C. As the temperature of the sample increases, absorbance of 260 nm light is monitored at 1° C. intervals, e.g. using a Cary (Australia) model 1E or a Hewlett-Packard (Palo Alto, Calif.) model HP 8459 UV/VIS spectrophotometer and model HP 89100A temperature controller, or like instruments. Such techniques provide a convenient means for measuring and comparing the binding strengths of antisense oligonucleotides of different lengths and compositions.

In yet another aspect, a pharmaceutical composition comprises a compound that inhibits the activity of the crc protein. Such compound can be identified by any of the methods described above.

Pharmaceutical compositions of the invention include a pharmaceutical carrier that may contain a variety of components that provide a variety of functions, including regulation of drug concentration, regulation of solubility, chemical stabilization, regulation of viscosity, absorption enhancement, regulation of pH, and the like. For example, in water soluble formulations the pharmaceutical composition preferably includes a buffer such as a phosphate buffer, or other organic acid salt, preferably at a pH of between about 7 and 8. For formulations containing weakly soluble antisense compounds, microemulsions may be employed, for example by using a nonionic surfactant such as Tween 80 in an amount of 0.04–0.05% (w/v), to increase solubility. Other components may include antioxidants, such as ascorbic acid, hydrophilic polymers, such as, monosaccharides, disaccharides, and other carbohydrates including cellulose or its derivatives, dextrins, chelating agents, such as EDTA, and like components well known to those in the pharmaceutical sciences, e.g. Remington's Pharmaceutical Science, latest edition (Mack Publishing Company, Easton, Pa.).

An effective amount of oligonucleotide for particular applications depends on several factors, including the chemical nature of the antisense oligonucleotide, the disorder being treated, the method of administration, and the like. Preferably, an effective amount will provide a concentration of oligonucleotide of between about 1 to 100 $\mu$M at the target polynucleotide; and more preferably, an effective amount will provide a concentration of antisense oligonucleotide of between about 1 to 10 $\mu$M at the target polynucleotide.

Depending on the structural and stability characteristics of the active compound, the per unit dosage and precise formulation of the pharmaceutical composition may vary. Typically, such compound would be administered orally at a dose ranging from 0.08 mg to 5 g daily, preferably between 0.2 mg to 0.2 g daily, most preferably between 0.8 mg to 100 mg daily. Preferably the compound would be administered multiple times per day and can be administered in a single dose, although this is less preferred. Typically, the drug delivery vehicle, whether liquid, gel, tablet, or another vehicle, will permit effective release of the compound at the site of infection. The drug delivery vehicle can provide for either immediate release or systematic release over time at the site of infection. The inhibitor compound can be administered parenterally, such as intravenously, but this is less preferred. The compound can also be administered prophylactically to prevent the onset of disease associated with bacterial infection.

The tablets, troches, pills, capsules and the like may also contain the following: a binder such as polyvinylpyrrolidone, gum tragacanth, acacia, sucrose, corn starch or gelatin; an excipient such as calcium phosphate, sodium citrate and calcium carbonate; a disintegrating agent such as corn starch, potato starch, tapioca starch, certain complex silicates, alginic acid and the like; a lubricant such as sodium lauryl sulfate, talc and magnesium stearate; a sweetening agent such as sucrose, lactose or saccharin; or a flavoring agent such as peppermint, oil of wintergreen or cherry flavoring. Solid compositions of a similar type are also employed as fillers in soft and hard-filled gelatin capsules; preferred materials in this connection also include lactose or milk sugar as well as high molecular weight polyethylene glycols. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye, flavoring such as cherry or orange flavor, emulsifying agents and/or suspending agents, as well as such diluents as water, ethanol, propylene glycol, glycerin and various like combinations thereof. Of course, any material used in preparing any dosage unit form should be pharmaceutically pure and substantially non-toxic in the amounts employed.

The present invention is explained in greater detail in the following non-limiting Examples.

EXAMPLE 1

Virulence of crc+ and crc−

*Pseudomonas aeruginosa* in a Mouse Burn Model

A wild-type strain of *P. aeruginosa* designated PAO0001, a crc point mutation strain of *P. aeruginosa* designated PAO8007, and a crc knock-out strain of *P. aeruginosa* designated PAO8020, were tested in a burned mouse model of bacterial virulence. 200 cells of the indicated strain were injected into the burned skin wound of the animals. At 48 hours post burn/infection death was observed in four of the five mice infected with PAO0001. Large numbers of PAO0001 were recovered from skin, blood, liver, spleen and other organs at death. This is similar to the mortality found in other strains of *P. aeruginosa*.

In contrast, only one of five animals infected with PAO8007 was dead 48 hours after burn and infection (again with 200 bacterial cells), and all four remaining animals were still alive 7 days after burn and infection. Similar results were seen with animals infected with PAO8020.

The foregoing study was repeated with PAO8007 and PAO8020, but ten times the usual amount of bacteria was injected into the burn wound (i.e., 2,000 bacterial cells per animal). Essentially the same results were seen.

EXAMPLE 2

Fluoroacetamide Plate Assay for Crc

This assay (described in O'Toole et al., *J. Bacteriol.* 182, 425–431 (2000)) takes advantage of the Crc mediated repression of the amidase operon of *P. aeruginosa* by organic acids. Amidase hydrolyzes the fluoroacetamide into the toxic intermediate fluoroacetic acid. The steps are as follows:

(1) streak bacteria onto a BSM minimal (W Lynch and M. Franklin, *Arch. Microbiol.* 118, 133–140 (1978)) plate containing 40 mM succinate and grow overnight at 37 degrees centigrade.

(2) Restreak bacteria onto BSM minimal containing 40 mM succinate and 2.5 mg/ml fluoroacetamide (FAA) (Aldrich 12,834-1). Incubate about 36 hours at 37 degrees. In crc+ strains, succinate represses the expression of amidase and allows for growth in the presence of FAA. Catabolite repression control—negative (crc-) mutant strains express amidase which converts FAA to the toxic intermediate fluoroacetate, hence the mutants do not grow.

The foregoing is illustrative of the present invention, and is not to be construed as limiting thereof. The invention is defined by the following claims, with equivalents of the claims to be included therein.

---

That which is claimed is:

1. A method of screening for compounds that inhibit the virulence of *Pseudomonas* bacteria, comprising the steps of:

providing a culture medium comprising *Pseudomonas* bacteria and a catabolite repression control (Crc) protein-mediated amidase operon repression, wherein the culture medium contains fluoroacetamide in an amount toxic to said bacteria in the absence of said Crc protein-mediated amidase operon repressor;

administering a test compound to said bacteria; and then detecting the poisoning of said bacteria by said fluoroacetamide and detecting the presence or absence of inhibition of the expression of the Crc protein in said bacteria, wherein the poisoning of said bacteria by said fluoroacetamide and the inhibition of the expression of said Crc protein indicates said test compound has antivirulence activity against *Pseudomonas* bacteria.

2. A method according to claim 1, wherein said *Pseudomonas* bacteria is selected from the group consisting of *Pseudomonas aeruginosa, Pseudomonas multivorans, Pseudomonas fluorescens,* and *Pseudomonas putida*.

3. The method according to claim 1, wherein said *Pseudomonas* bacteria is *Pseudomonas aeruginosa*.

4. The method according to claim 1, wherein said amidase operon repressor is selected from the group consisting of Krebs cycle intermediates and acetate.

5. The method according to claim 1, wherein said Crc protein-mediated amidase operon repressor is succinic acid.

6. The method according to claim 1, wherein said step of detecting the poisoning of said bacteria is carried out by detecting cell death or inhibition of cell growth.

7. The method according to claim 1, wherein said test compound is a member of a combinatorial library.

8. The method according to claim 1, wherein said test compound is selected from the group consisting of small organic compounds, oligomers and combinations thereof.

9. A method of screening for compounds that inhibit the virulence of *Pseudomonas* bacteria, comprising the steps of:

providing a culture medium comprising *Pseudomonas* bacteria;

administering a test compound to said bacteria; and then detecting the presence or absence of inhibition of the expression of a catabolite repression control (Crc) protein in said bacteria, the inhibition of the expression of the Crc protein indicates said compound has antivirulence activity against *Pseudomonas* bacteria.

* * * * *

UNITED STATES PATENT AND TRADEMARK OFFICE
CERTIFICATE OF CORRECTION

PATENT NO. : 6,824,979 B2
DATED : November 30, 2004
INVENTOR(S) : Phibbs et al.

It is certified that error appears in the above-identified patent and that said Letters Patent is hereby corrected as shown below:

<u>Title page,</u>
Item [57], ABSTRACT,
Line 5, should read -- compound to the bacteria, and then detecting the presence --

<u>Column 11,</u>
Line 17, should read -- protein-mediated amidase operon repressor, wherein --

<u>Column 12,</u>
Line 11, should read -- 4. The method according to claim 1, wherein said ami- --

Signed and Sealed this

Twelfth Day of April, 2005

JON W. DUDAS
*Director of the United States Patent and Trademark Office*

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic oligonucleotide

<400> SEQUENCE: 1
ccgcgctcgg ccgcagcctg                                          20

<210> SEQ ID NO 2
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic oligonucleotide

<400> SEQUENCE: 2
ggtagcgccc gtaacgatcg gccg                                     24

<210> SEQ ID NO 3
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic Oligonucleotide

<400> SEQUENCE: 3
ccgttcgggc gcgaggaagc ccgg                                     24

<210> SEQ ID NO 4
<211> LENGTH: 22
<212> TYPE: DNA
<213> ORGANISM: Artificial Sequence
<220> FEATURE:

-continued

```
<221> NAME/KEY: misc_feature
<222> LOCATION: (1)..(22)
<223> OTHER INFORMATION: Synthetic oligonucleotide

<400> SEQUENCE: 4
gaagcggcgt aggccggggg tc                                        22
```